United States Patent
Budd et al.

(10) Patent No.: US 7,430,047 B2
(45) Date of Patent: Sep. 30, 2008

(54) SMALL CONTAINER FLUID DYNAMICS TO PRODUCE OPTIMIZED INSPECTION CONDITIONS

(76) Inventors: Gerald Walter Budd, 36853 Heatherton Rd., Farmington, MI (US) 48335; Julius Z. Knapp, 22 Foxwood Dr., Somerset, NJ (US) 08873

( * ) Notice: Subject to any disclaimer, the term of this patent is extended or adjusted under 35 U.S.C. 154(b) by 344 days.

(21) Appl. No.: 11/076,375

(22) Filed: Mar. 9, 2005

(65) Prior Publication Data

US 2005/0248765 A1    Nov. 10, 2005

Related U.S. Application Data

(60) Provisional application No. 60/551,562, filed on Mar. 9, 2004.

(51) Int. Cl.
*G01N 21/90*    (2006.01)
(52) U.S. Cl. .................................. 356/427
(58) Field of Classification Search ............. 356/427, 356/335, 338
See application file for complete search history.

(56) References Cited

U.S. PATENT DOCUMENTS 6,498,645 B1 * 12/2002 Knapp et al. ............. 356/427

* cited by examiner

*Primary Examiner*—Roy M Punnoose (57) ABSTRACT

New methodology, realizable with both manual and new semi-automatic imaging technology, has transformed both the inspection and the batch release Attribute Sampling Inspection for contaminating visible particles in injectable solutions into statistically replicable procedures. In this new non-destructive inspection procedure, a calibration curve relates NIST traceable measurement of maximum particle size to the rejection probability of the particle. Data for this calibration curve is determined with a graduated set of single durable stainless steel and glass microspheres that are sized with NIST traceability. Use of the calibration curve transforms the probabilistic variability of visible particle inspection data described by Knapp into the 'simply replicable form' required by the Attribute Sampling Tables. The present invention uses cutting edge imaging technology to achieve 1% sizing accuracy within 10 μm from 50 to 1,000 μm. An improved alternative sizing technique used in this invention uses the particle information to achieve an integral particle sizing function.

18 Claims, 5 Drawing Sheets

Elapsed Time

Figure 7
Calibration Curve NIST Traceable Particle System [40 μm to 300 μm Diameter SS spheres]

Figure 8
Large Particle (>550 ms Acquisition)

SMALL CONTAINER FLUID DYNAMICS TO PRODUCE OPTIMIZED INSPECTION CONDITIONS

CROSS-REFERENCE TO RELATED APPLICATIONS

I claim priority to my Provisional Patent Application No. 60/551,562 with filing date Mar. 9, 2004.

FIELD OF THE INVENTION

This invention relates to the procedures and devices utilized in the optical inspection of transparent containers for the presence of contaminating particulate matter and particularly to inspection of injectable pharmaceutical preparations.

BACKGROUND OF THE INVENTION

The inspection for and elimination of visible particle contaminated containers from a batch of injectable pharmaceuticals is a United States Pharmacopeia requirement. This inspection is specified to be, whenever possible, after the product is in its final container. Evaluation that the visible particle incidence rate is within USP acceptance limits for human or veterinary use is an essential part of the injectable batch release procedure. It is also an essential prerequisite to the continuous improvement of the quality of an injectable product batch and to the reduction of product cost. These ends have been achieved by incorporating advances in behavioral science, physics and biophysics, illumination and mechanical engineering, pharmaceutics and statistics into a single analytical structure.

Any proposed inspection for visible contaminating particle size in an injectable product, manual semi-automated or fully automated must be validated before it can be used on a United States Pharmacopeia (USP) listed product. Validation in this Good Manufacturing Practices (GMP) sense means that it must be demonstrated to be at least as effective as the preceding method or mechanism. The preceding method of inspecting injectable products for contaminating particles was the inspection of single containers by clinical staff at the injection site.

As shown by one of the authors in several papers, visible contaminating particles are randomly distributed throughout the batch. As such, a validated 100% inspection is essential to achieve accurate, sensitive contaminating particle incidence rate results. The use of the Attribute Sampling Inspection Tables with raw visible particle inspection data results in the incorrect rejection of good batches and incorrect acceptance of undesirable batches. The use of the Knapp-Abramson analysis framework provides the methodology, which transforms raw visible particle inspection data into a form acceptable to the Sampling Tables. For general use, the sensitivity and accuracy of the batch reject rate makes its use more desirable than decisions reached with the model based Sampling Inspection. Although the use of Attribute Sampling Assay Tables can be made compatible with raw visible inspection data, its limited sensitivity and the need to interpret the probability of the results obtained may very well shrink its future use to that of an investigators tool.

The authors of this inventions have been issued several patents in this field of study to aid the in the detection of particles in solutions. U.S. Pat. No. 6,498,645 describes a method for substantially complete detection of all particles, within a predetermined size range, contained in vessel containing an injectable solution. The method measures the blur fringe of particles as they move past the sensor in region near the inner wall of the container.

An improved technology was developed in 2003 the described a unique illumination and optical image system that increased the sensitivity of the detection system, currently the patent is pending (patent application Ser. No. 10/981,801, filed Nov. 5, 2004). The illumination technique and the detector-viewing angle allowed the inventors to examine the complete contents of the container being inspected. The technology allowed the system to identify heavy contaminating particles resting of the bottom of container, something that was not possible using previous technology. The introduction of a visible particle standard set in which the dimensions of the progressively sized single particles are traceable to the primary dimensional standards maintained by NIST makes possible the generation of a calibration curve. This calibration curve relates particle size to particle detectability providing a stable, transportable, national and international reference standard of particle visibility.

The conversion of the prime particle visibility parameter from detection probability to the measurement of particle size results in a measure better suited to continuous monitoring and quality adjustments in a production environment.

Combining NIST traceable sizing of stable microspheres with statistically accurate determinations of their rejection probability has made possible realization of a calibration curve relating the probability of manually detecting a contaminating particle to its NIST traceable maximum physical size. With USP acceptance and use of this calibration curve, inspection sensitivity and discrimination can both be defined and securely evaluated. This means that the basic manual inspection at all producing sites, and therefore the validated capability of any contaminating particle inspection method or mechanism, can now be evaluated on a level playing field. The availability of secure statistically reproducible contaminating particle data makes possible the on-going cycle of parenteral production line process improvements envisioned in Process Analytical Technology (PAT) publications.

BRIEF SUMMARY OF THE INVENTION

It is an object of the present invention to transform the present probabilistic detection of contaminating particles present in a container, even larger than 30 mm in diameter, into a deterministic detection and accurate measurement process.

It is a further object of the present invention to provide a method to position the particles in solution in a well-defined volume in the container to enhance the detection and measurement of contaminating particle(s).

It is a further object of the present invention to provide a method to define the mechanical requirements to produce the capability of positioning the particles in the defined inspection volume.

It is a further object of the present invention to define a "Velocity Motion Profile" that will optimize the fluid dynamics of the system so to reproduce the position of the particles in the inspection volume.

It is a further object of the present invention to define the concept of a unique "Velocity Motion Profile" for each inspection system based on the size and shape of containing vessel, the amount of fluid fill in the container and the viscosity of the fluid containing the contaminating particle(s).

It is a still further object of the present invention to provide a method to indicate the type of contaminating particle (based on density).

It is another object of the present invention to provide a method for construction of an accurate instrument calibration curve (actual particle size vs. apparent particle size in image) that is unique for each inspection system. The system includes the necessary mechanical and electrical hardware, software, and velocity motion profile and physical characteristics of the product being inspected.

Generally the present invention provides an improved method for the detection and measurement of all particles, within a predetermined size and density range, contained in an injectable solution, in a transparent container.

A short description of the mechanical and optical equipment used in the inspection device is provided here. A more detailed description and drawing of the apparatus is contained in U.S. patent application Ser. No. 10/981,801 filed on Nov. 5, 2004. The '801 patent applications' primary concern is that of the physical devices used to illuminate and acquire images of the particles. The present invention is describes a method to position the particle in the container for a more accurate measurement of size.

The method comprises the steps of:
a) pre-positioning particles in the container whereby rotation of the container causes substantially all of the particles in the injectable solution in the container to rotate, with approximately equal initial velocity, in a shell volume adjacent the inner walls of the container, with said shell volume having a predetermined thickness;
b) as more energy is imparted in the velocity motion profile the fluid will experience a toroidal motion in which fluid will move along the container bottom toward the center of axis of rotation, upward along the axis of rotation and then downward along the container walls;
c) the proper velocity motion profile will cause the migration of particle from the inner wall of the container toward the center of the container;
d) the degree of migration of the particle is directly related to the mass of the particle, heavy particles will migrate only slightly away from the wall, particles with less mass will migrate toward the bottom center of the container, and particles with the least mass will be moved to the center of the container and lifted from the floor of the container;
e) it is desirable to use a velocity motion profile that will position particles in the mass range being studied in a small volume on the bottom of the container at the center of rotation, referred to as the optimized inspection volume (OPTIV);
f) illuminating all the particles within the optimized inspection volume with lighting means;
g) detection of particles by movement on the container bottom and in solution by orienting the sensor with a downward angle with respect to the axis of symmetry of the container;
h) detecting at least one of light scatter, light reflection and light extinguishing caused by said particles, with detector means having a depth of focus of detection in which said particles remain in near-focus within the optimized inspection volume of the container; and
i) measuring at least one of light scatter, light reflection and light extinguishing caused by said particles, with detector means having a depth of focus of detection in which said particles remain in focus within the optimized inspection volume of the container.
wherein the sensed signal is corrected for the asymmetries of the imaging system by correction means either by computation or by repositioning the detector means relative to the container, whereby a focused imaging plane is formed at the container axis and then mechanically or electro-mechanically offset closer to the imaging sensor than the center of the cross section, whereby the size of detected particles in the opposite volumes is accurately mathematically compensatible to an actual size. The lighting means provides a multiplicity of directed light emitting diodes (LED's), mounted on three of the interior walls of a cubic structure with an acrylic element placed in the center. The diffusing element has a "U" shaped channel removed along the centerline of cubic structure in which the container being tested is positioned. The "U" shaped diffusing element is designed to uniformly diffuse the light entering the container. The sample container rest in slightly recessed pocket centered on a rotational device. The center of the axis of rotation is positioned to coincide with the center of radius and width of the "U" shaped channel in the diffusing element. The lighting means may be adjusted to enhance the image characteristics by activating various LED lighting elements within the structure. Contaminating materials with less optical density can be enhanced in the image by reducing the radiant energy of the illumination system.

With said detector being mounted inside a sealed enclosure the critical optical components of the system can be protected from the environment. The detector is mounted in such a manner so that so that the optical path can be easily adjusted with the target area. The design of the sensor enclosure allows for the insertion of optical filter elements within the optical path of the invention.

These and other objects, features and advantages of the present invention will become more evident from the following discussion and drawings in which:

DETAILED DESCRIPTION OF THE INVENTION

Figure 1:
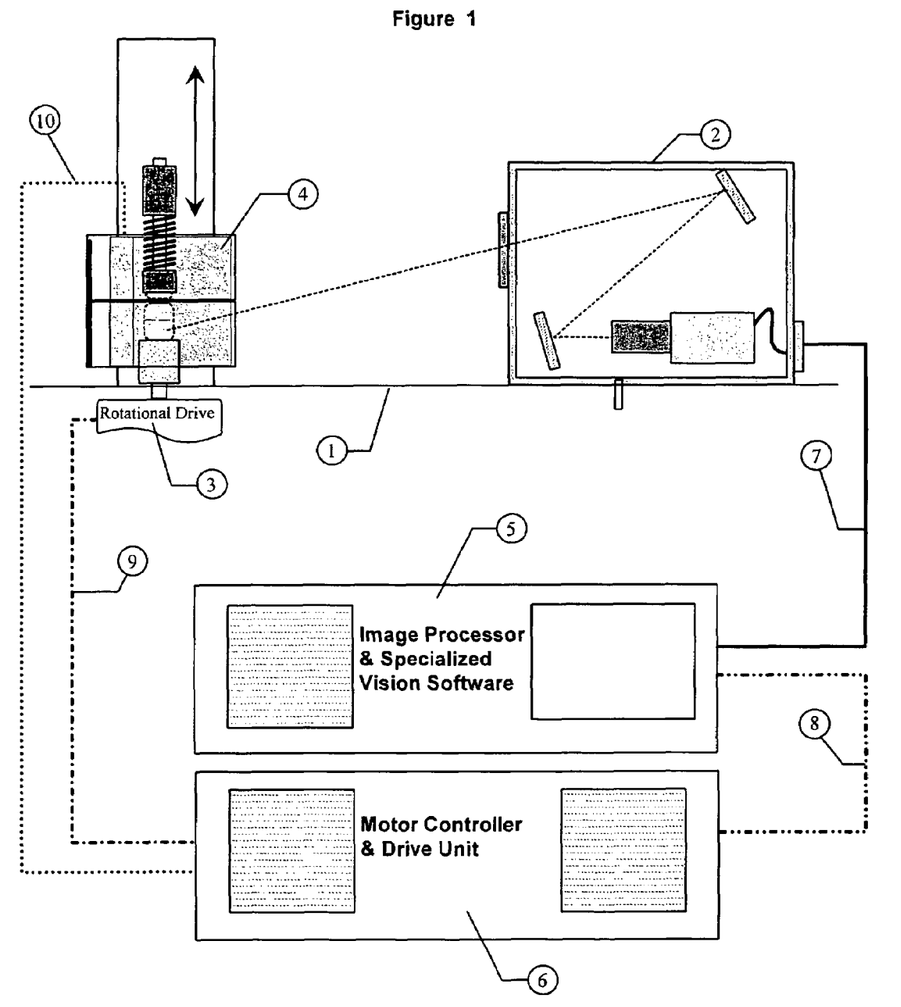
FIG. 1 illustrates the major components necessary to the invention to function and their relative position with respect to each other.

The invention is a combination of mechanical, electronic, and software components configured in the proper way to produce information that will yield repeatable measurement results. The major components and their relationship to each other are illustrated in FIG. 1. The alignment of components used for image acquisition is very important and must be referenced to level surface (item 1). A machined surface provides a excellent datum for mounting the sensor module (item 2), the rotational drive (item 3) and the illumination module (item 4). Item 2 through 4 are described in detail in the U.S. patent application Ser. No. 10/981,801. The sensor module contains the sensor, relay mirrors (if required), and filter elements (if required) and a method to maintain the orientation of the components with respect to each other. The sensor module was designed so that it could be replaced as a whole with a nearly identical module. The physical dimension of the sensor module would be identical but the electronics (sensor) may not have exactly the same characteristics and therefore would have a different response/calibration curve. By adjusting the inspection parameters to match the calibration curve the modules will produce the same measurement capabilities. The rotational drive (item 3) is a low inertia motor that is capable of accelerating and decelerating very quickly. The motors are tested and matched so that they can also be replaced should a failure occur. The motor rotates the container around a central axis so to put the fluid in motion.

The illumination module (item 4) is a Phoenix Imaging, Ltd. design and provides very uniform lighting conditions within the containers being tested. The illumination module provides diffuse illumination from multiple directions using special surface mount LED panels. The panels can be turn on or off as required for the various stages of the inspection. The stages of the inspection will be discussed later in this description. The illumination system is moved on a linear translation stage that allows it to move up and down along the axis of rotation. The illumination module translates up so that it exposes the entire test container. This makes it easy to load and unload the containers for testing. The illumination module, like the sensor module is constructed so that it can be replaced as a whole should a failure occur. The illumination modules are machined to exacting standards to insure that each unit is virtually identical.

The entire concept of this invention is based on the interchangeability of components in the system. The mechanical components will experience the greatest physical stress and are designed to allow quick replacement of components when implemented in a production environment. The present invention allows the modules to be pre-calibrated so that they can be used in the equipment and validated for operations quickly. The electronic components used to control the surface mounted devices, that is, the sensor and illumination modules are also modular in design. The image processor with specialized vision software (item 5), acts as the cell controller and is responsible for analysis of the data. The image processing hardware is constantly evolving with faster central processing units, faster memory, and faster computer bus speeds. The core inspection algorithms are designed maximum efficiency and can extract information for measurements very quickly. The image processing function will continue to experience a decreased in the time required for analysis of the images with little need to change the vision algorithms. The motor controller and Drive Unit (item 6) is responsible for performing the predetermined velocity motion profile. The motor controller also has the responsibility for controlling the illumination module.

All of these devices have interconnections that allow each device to communicate with associated devices. The connection between the sensor module and image processor is indicated by item 7. All of the functions the sensor module is capable of performing are controlled by the image processor, including sensor and filter control. The interconnection between the image processor and the motor controller is a serial data link (or Ethernet) indicated by item 8. The connection to the motor from the drive unit is a hard cable and is indicated by item 9. The illumination module is controlled by a link (item 10) from the motor controller.

The function of all the components listed about is to generate a method to rotate a container using a predetermined velocity motion profile so that the particles will migrate to a location in the container so that the system can detect and accurately measure the size of particle. The image analysis has been previously described in the '801 patent application. The image processing technique has been revised to provide better contrast between the particle and the container background. The image processing is now divided into "n" number of inspections, typically three inspection algorithms are employed. The first is the initial "Light (low density) Particle Inspection" which occurs just prior to or immediately after the "light particle velocity motion profile". Low-density contaminating particles generally require very little energy to cause them to move. The inspection system detects the movement of the particle and uses the translation information to calculate the particles' path in the solution. The images are acquired at the necessary rate to "track" the particle from one position to the next. The vision algorithm will ignore subtle changes in the image background and enhance the information of a moving object (particle). The number of images acquired for the analysis of the "Light Particle Inspection" is user selectable, a typical number of images will vary between 6-20.

After the images have been acquired the system will perform the "velocity motion profile" for the specific characteristics of the samples being inspected. The velocity motion profile is specific for the size, shape, fill volume (level of fluid placed in the container), surface tension and the viscosity of the fluid in the container. The velocity motion profile is mentioned here because the combination of physical attributes describe a non-linear velocity system and their control is critical to the successful implementation of the present invention. The individual velocity motion profiles are considered a "trade secret" by the inventors and will not be disclosed in this application. For the purpose of demonstrating how the velocity motion profile is used in the present invention we will provide "Velocity Motion Profile W1" for Water for Injection (WFI) placed in a 22 mm diameter, 5 ml container, with a 3 ml volume fill. The actual profile and shape will be discussed shortly.

Figure 2:
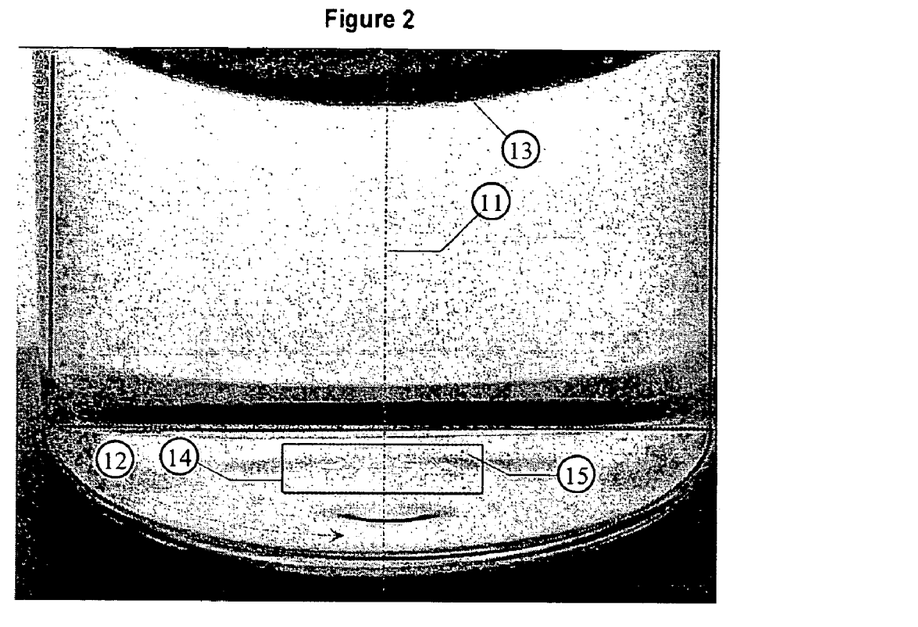
FIG. 2 illustrates an image acquired after the completion of a normal velocity motion profile.

When the velocity motion profile is executed properly the fluid dynamics are such that a predictable and uniformly smooth meniscus. FIG. 2 illustrates the conditions that yield a successful determination of particle size using the present invention. The container is rotated about a central axis of rotation (item 11). The axis on rotation should coincide with the axis of symmetry of the container. If the two axes do not coincide the risk of turbulent fluid flow is greatly increased. The container may be rotated either direction, when rotated in a counter-clockwise direction the fluid flow will be from left to right along the front interior surface. Item 12 indicates the preferred direction of fluid flow. The smooth meniscus is illustrated by item 13 and represents a parabolic shaped interface between the fluid and the air in the container. When the proper velocity motion profile is employed the location of the particle(s) can be shown to reside in a well-defined volume centered on the bottom of the container. Item 14 represents the approximate frontal area of the inspection volume with respect to the size of the container. Item 15 indicates the presence of a 100 μm stainless steel sphere after the running the velocity motion profile.

Figure 3:
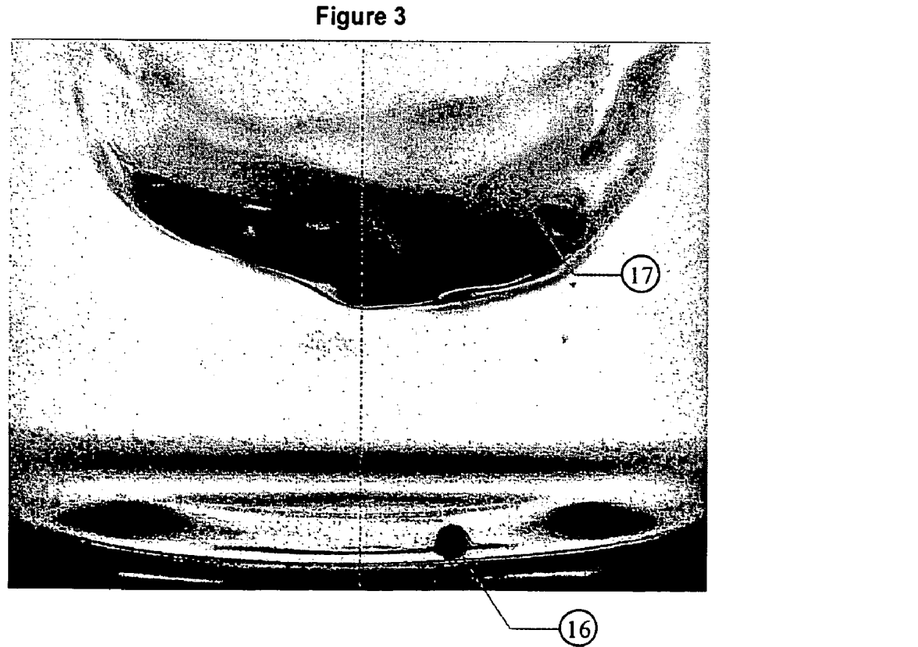
FIG. 3 illustrates an image acquired after turbulent meniscus was generated by an unacceptable velocity motion profile.

More energy is required by the system to set large particle in motion. Item 16 in FIG. 3 represents a 1000 μm diameter stainless steel sphere. A particle of this size is a very heavy particle, defining the upper mass limit of any contamination that would be found in pharmaceutical operations. This upper limit provides that any particle of less mass would be placed in motion with the velocity motion profile and is used for here for calibration purposes in the present invention.

FIG. 3 illustrates the typical result of a turbulent velocity motion profile. There are two important limitations to the transfer of motion to any contaminating particle. The first is the creation of cavitation. Cavitation is created when the acceleration or deceleration rates used to transfer movement to the visible particle contaminants that are to be detected exceed the cavitation onset threshold. The bubbles that are created when cavitation occurs cannot be efficiently separated from particle images and are therefore an interference to the accuracy of an inspection. The second limitation is the avoidance of turbulent flow in the meniscus as shown in FIG. 3. The cavelets in the meniscus, visible as item 17 in FIG. 3, act as mirror lenses and project focused reflections of the light source on the walls of the container. These light spots are interpreted as false contaminating particles that result in false container rejection and must be avoided in a successful inspection method. In present art this is accomplished by either a) delaying the start of the inspection until any turbulent meniscus movement has decayed to the smooth laminar shape shown in FIG. 2 or b) masking the image of the meniscus from inspection. An undesired effect of the inspection period delay, a), is that the duration of the effective inspection period in which the contaminating particle is in motion has also been shortened. The effect of selecting b) is a reduction in the maximum probability of particle detection to the proportion of volume scanned thus reducing the effectiveness of the inspection. The maximum particle detection probability cannot exceed the proportion of the container volume that is inspected.

Figure 4:
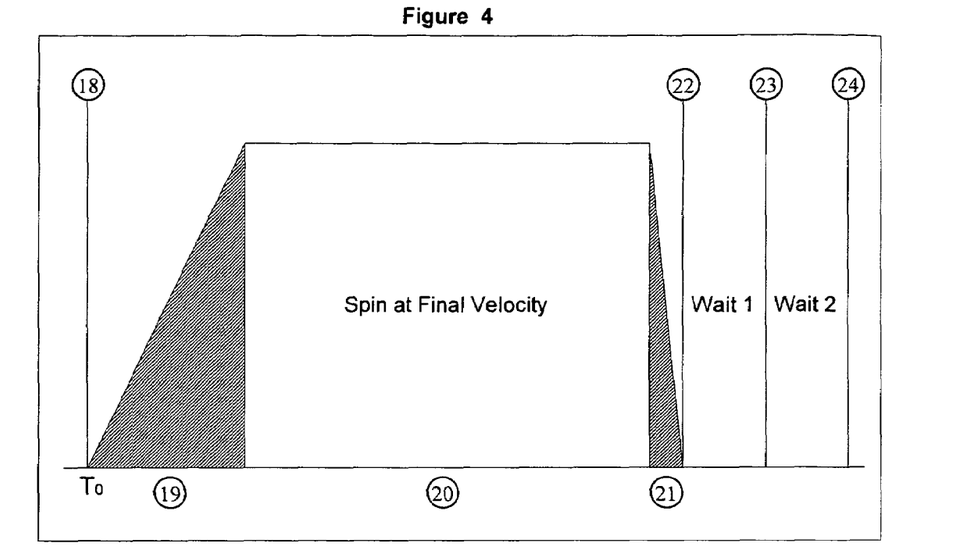
FIG. 4 diagrams the general characteristics of a velocity motion profile.

FIG. 4 illustrates the typical characteristics of a velocity motion profile. The velocity motion profile begins at to indicated by the first vertical line (item 18). The acceleration rate, (indicated by item 19), is defined by either the motor acceleration (revolutions per second$^2$) or by the time required to reach the containers' final spin or angular velocity ($V_t$). The final spin velocity is defined in revolutions per second and is indicated in FIG. 4 as item 20. The deceleration phase is indicated by item 21 and is the time required for the container to reach the angular velocity of zero ($V_0$). The deceleration is defined as motor deceleration (negative revolutions per second$^2$) or time required for the container to stop from the final spin velocity to a velocity of zero. The line indicated by item 22 is the mark when the container has reached the velocity of zero after the spin. The time elapsed between the mark at item 22 and the mark at item 23 is the delay time. The line indicated by item 23 is the image acquisition point and it is the time after $T_0$ when the system will begin acquiring images.

More than one image acquisition point may be used in the inspection sequence. It is typical to employee at least two such points in the analysis of a container. The first image acquisition point would be located on the velocity motion profile for the detection of low mass materials. The second image acquisition point (represented by the line item 23) would occur immediately after or short after the container velocity has reached zero and is used to isolate very large or heavy particles with a rapid settling time, such as large metal fragments or glass shards. Another image acquisition point (represented by line item 24) would be positioned to detect smaller particles in the heavy to medium heavy mass range. This third delay may occur several hundred milliseconds after the container has reached zero velocity.

The overall shape of the velocity motion profile is critical for inducing motion in contaminating particles while maintaining a uniform shape to the meniscus. This invention utilizes an optimized velocity motion profile for detecting and measuring stainless steel spherical particles in WFI. This profile will position all particles within defined inspection volumes if they have a density in the range of 0.95 gm/cc to 8.2 gm/cc. The heavy particles such as stainless steel (density 8.2 gm/cc) are more difficult to place in motion than particles with less density. Typical velocity motion profile a 5 ml Small Volume Injectable container with 3 ml fill level are 4 to 6 milliseconds acceleration and deceleration phases to and from a constant speed phase of 2,200 to 2,500 RPM for 150 to 400 milliseconds.

Figure 8:
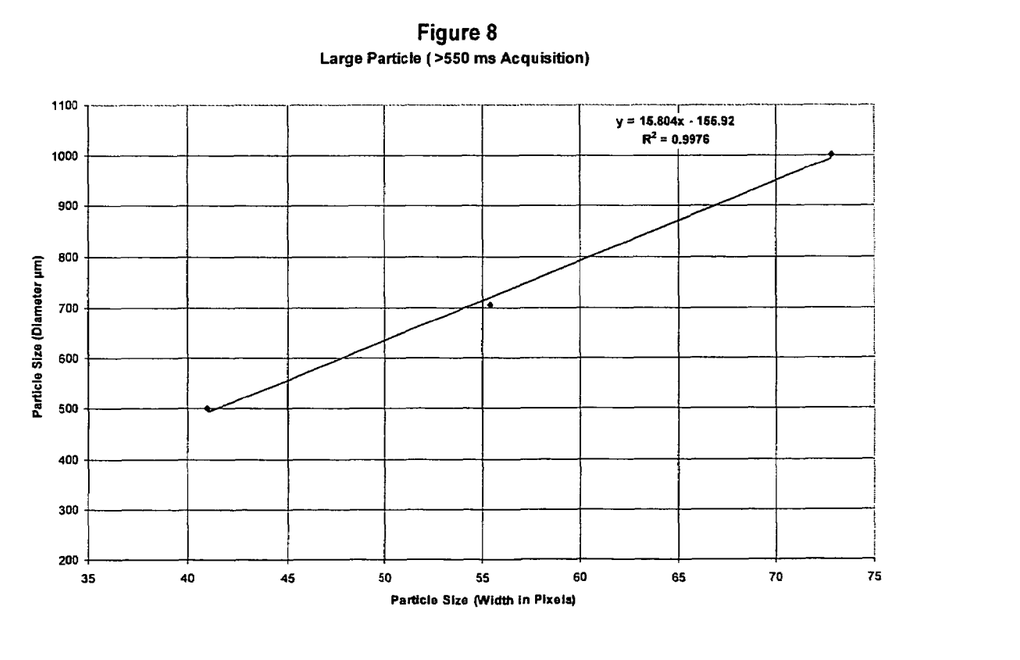
FIG. 8 illustrates the resulting calibration curve for large particles (diameter >500 μm) using the velocity motion profile for WFI.

The current invention allows the definition of multiple inspection volumes, each of which can have a unique inspection vision algorithm and analysis algorithm associated with it. This case is effectively illustrated by FIG. 3 in which the velocity motion profile has set a 1000 μm diameter stainless steel sphere into motion. Although the velocity motion profile has generated turbulent fluid flow and distorted the meniscus, the present invention isolates and measures the particle size in an inspection volume defined near the lower front interior volume of the container. The volume can be represented as 75° slice of an annular ring with an inner diameter of 0.8 times the container diameter and extending to containers' interior wall with a height of approximately 2.5 mm. In this wedge shaped inspection volume the particles will travel from left to right when a counter-clockwise velocity motion profile is used. The particle can be size accurately using a calibration curve specific to this inspection volume, see FIG. 8.

Figure 5:
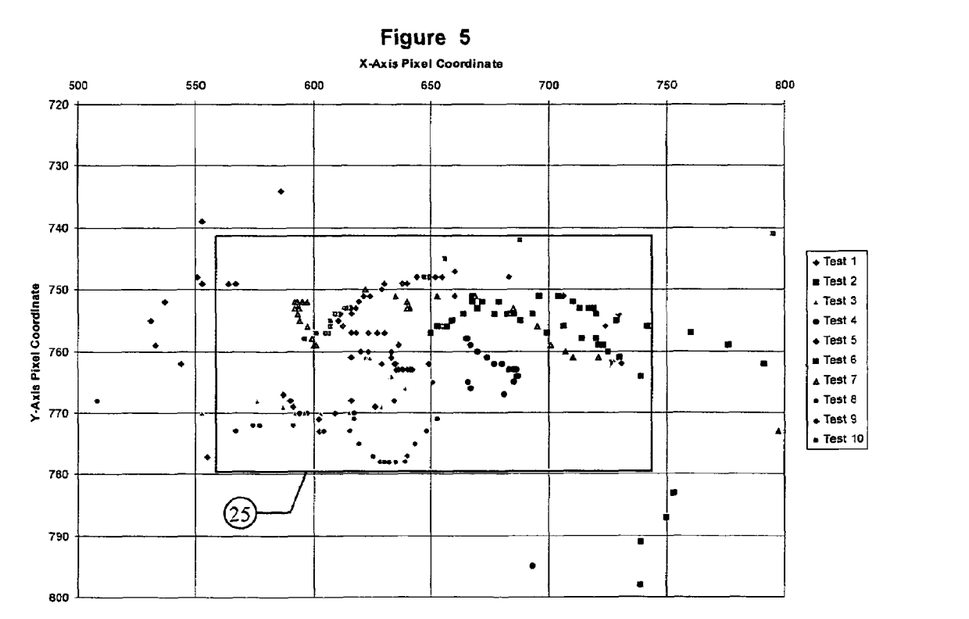
FIG. 5 illustrates the path a 100 μm particle follows after an acceptable velocity motion profile.

FIG. 5 illustrates the ability of the present invention to position a 100 μm particle in the defined inspection volume in a repeatable manner. The velocity motion profile insures that the particle will be present in the inspection volume during the testing period. After the inspection period has concluded the particle may migrate outside the inspection volume. FIG. 5 is a plot of a small region of the sensor's array. The sensor used in this setup has a size of 1300 horizontal pixels×1030 vertical pixels. FIG. 5 represents the portion of the array between 500 to 800 horizontal pixels and 720 to 800 vertical pixels. The image area is defined with the origin being located at the upper left corner of the array, increasing pixel positions go from left to right and top to bottom. The plot illustrates the path of particle motion for 10 individual runs. In each case the container was removed from the apparatus after each run. The general pattern illustrates that particles begin their motion near the inner wall of the container and move toward the bottom center of the container. The box labeled item 25 in FIG. 5 is the inspection volume where the particle will finish its motion. This box has dimensions of 180 pixels wide by 40 pixels high. The plot clearly demonstrates the ability to position the particles in a well-defined inspection volume. The present invention has the ability to position particles with a density of 0.95 to 8.2 gm/cc with a diameter of 350 μm or less within the defined inspection volume. This can be illustrated by the linearity of the calibration curve generated for particle in that size range, see FIG. 7.

Figure 6A:
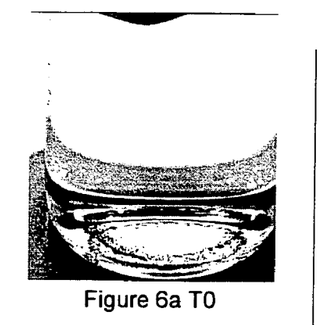
FIG. 6 is a series of eight images that document the movement of 100 μm diameter carbon spheres using a predetermined velocity motion profile.
Figure 6B:
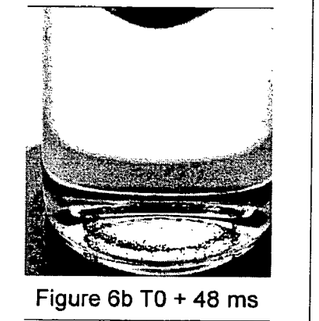
Figure 6C:
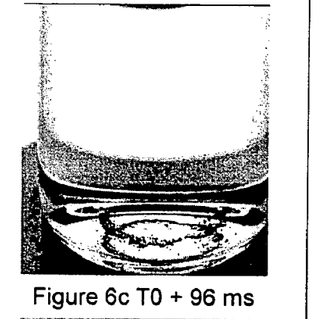
Figure 6D:
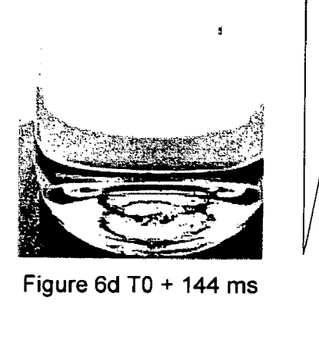
Figure 6E:
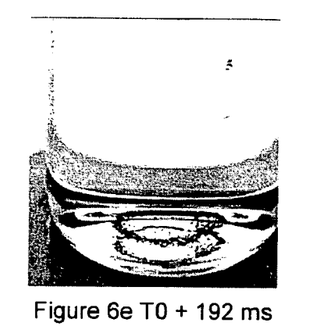
Figure 6F:
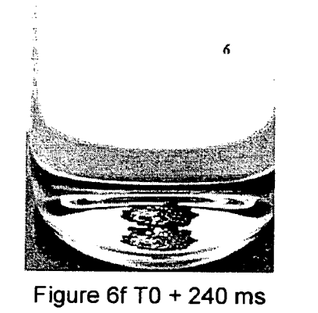
Figure 6G:
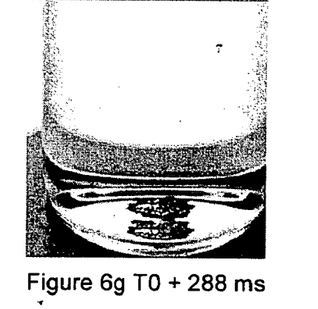
Figure 6H:
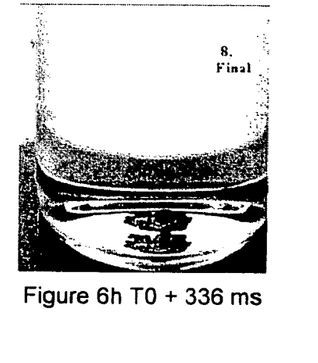

The general shape of the particle path as generated by the predefined velocity motion profile shows a collapse of the particle position toward the center of the container. This is further illustrated by FIGS. 6a through 6h. In this experimental setup the same velocity motion profile for WFI was used with a container seeded with 100 μm diameter carbon spheres. The image acquisition begins at $T_0$, which occurred approximately 150 milliseconds after the container reached zero velocity. FIG. 6a is the first image in the sequence that the spheres are spread out in a ring pattern just in from the interior container wall. As the image sequence progresses, the spheres begin to collapse toward the center of the container.

About 192 milliseconds after the initial image the ring has collapsed to about half its initial diameter. At the conclusion of the image sequence the spheres have amassed in the center of the container and begin to pile on top of each other forming a peak. The images in FIG. 6 clearly demonstrate the true motion of particles in a container rotated with a velocity motion profile of sufficient energy to put them into motion. Contrary to the popular belief that centrifugal force will keep the particle near the container wall it is clear shown that a toroidal fluid flow in the container will move them toward the center of the container after the rotation has stopped.

Figure 7:
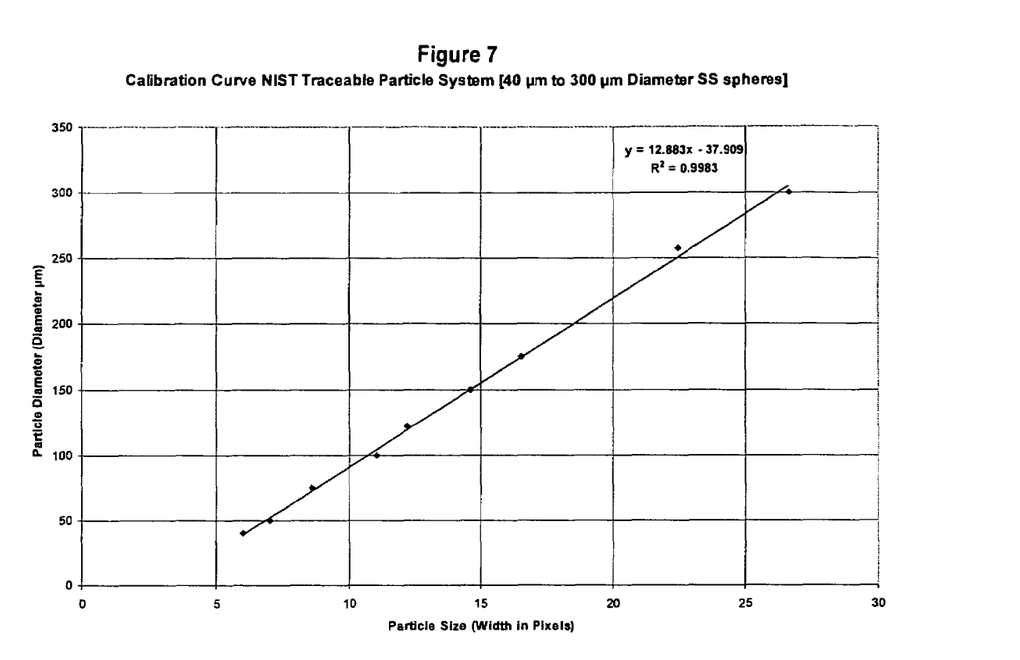
FIG. 7 illustrates the resulting calibration curve for small particles (diameter <350 μm) using the velocity motion profile for WFI (Water for Injection)

The most important feature of the present invention is its ability to generate a linear calibration curve corresponding to each inspection volume. FIG. 7 show the calibration curve central inspection volume using the WFI velocity motion profile. The curve was generated using a standard calibration set constructed using NIST traceable stainless steel spheres with a diameter range from 40 μm to 300 μm. The calibration curve is linear with an $R^2$ valve of >0.998. This calibration curve allows the present invention to determine the diameter of a particle in the center inspection volume to ±10 μm. The present invention can perform simultaneous independent evaluation of near-field and far-field images. The ability to size particles in the inspection volume to that accuracy provides a method that makes NIST traceable maximum particle size measurements possible with the generation of a calibration curve relating the probability of detecting a particle to its physical size. When this calibration curve is determined with microspheres that have been inspected under standard conditions (light quality and intensity, manipulation of the container, duration of the inspection, the background employed) and sized with NIST traceability, the basis for an accurate international standard of particle contamination quality has been established.

The standard (particle size)/(particle rejection probability) calibration curve can be considered an equivalent to the use of the set of standard microspheres used to calibrate particle counters. The probability that similar microspheres will be found in a biological or chemical suspension is small. The microspheres in the calibration sample are used to determine that the functionality of the visible particle inspection method or system has the sizing accuracy desired.

The U.S.P. United States Pharmacopeia (U.S.P.) designates the effectiveness of the manual inspection, which is available up to the moment of clinical use, as the benchmark inspection performance required. Any alternative inspection must be shown to be as effective as the benchmark manual inspection before it can be used on a U.S.P. listed product. The improvement described in the present invention applies to both the benchmark manual inspection as well as to semi- and fully automated contaminating particle inspection methods and mechanisms described herein.

What is claimed is:

1. An improved apparatus with diffuse backlight illumination system for the accurate detection and measurement of key characteristics of moving particles in the solution of small containers, 1 ml to 50 ml, with a machine vision measuring system comprising:

a) an image processing computer for image acquisition, image storage, image processing capability and analysis of images or derivations of images;

b) the image processing computer comprising memory for storing the images formed by the camera or cameras;

c) the image processing computer also comprising digital parallel input/output digital serial, and Ethernet communication capabilities for providing messages to external devices to report one or more measurements or characteristics of the particles in the solution that have changed in position the stored images;

d) the image processing computer executing control software stored in a computer readable medium, for allowing request and response signals from external devices indicating the parameters required for the inspection of a specific container type, for causing the image processing computer to perform image alignment and analysis for extraction of key characteristics of particles in the solution that have changed position within the container;

e) the image processing computer executing control software stored in a computer readable medium, for allowing request and response signals from external devices causing the image processing computer to store a reference image of container and the solution within the container without the detection of any contaminating particles in the solution in a memory location referenced by a specific identification code that is unique to the container model, type, specific contents and fluid fill level;

f) the image processing computer executing control software stored in a computer readable medium, for allowing request and response signals from external devices causing a determination of the exact position of the container by extracting one or more edges of the container based on grayscale information for causing the image processing computer to accurately position the inspection zones;

g) one or more image sensors with lens that provides a spatial resolution of 15 to 25 micrometers per pixel and depth of field necessary to form a sharp focus image of substantially all of the bottom interior surface of the container or a target portion thereof including the meniscus;

h) wherein each image sensor comprises the pixel resolution to resolve a contaminating particle of at least 20 micrometers in diameter resting on the interior bottom center of the container;

i) a minimum of one set of optical components are aligned so that the optical path is at a downward angle less than perpendicular from the axis of rotation permitting the sensor to view substantially all of the bottom interior surface of the small container;

j) an optional second set of optical components are aligned so that the optical path is at an angle perpendicular from the axis of rotation permitting the sensor to view half of the fluid volume and half of the lower surface of the fluid meniscus within the container;

k) an illumination system comprised of a cube structure with a "U" shaped channel cut into an optical grade polycarbonate or acrylic cube, and is machined so that the center of the "U" channel coincides with the axis of rotation of the container, with the diameter of the channel allowing the container being inspected to fit inside without interference with the channel walls;

l) the illumination system implements high density of light emitting diodes (LED's), a minimum of 4 LED's per square centimeter, arranged around the perimeter of the diffusing cube and is positioned to uniformly illuminate the contents of the container;

m) the illumination system utilizing one or more precision power supplies with control circuitry to turn on or off sections the LED's as required by the image processing system to enhance the contrast of the particles in the solution of the container;

n) a precision drive motor is connected directly to recessed bottom container holder is used to impart rotational motion to the base of the container in a precise and repeatable manner with a motion processing computer and drive unit comprising memory for storing one or more defined motion programs;

o) the motion processing computer also comprising digital parallel input/output digital serial, and Ethernet communication capabilities for providing messages to external devices to report status of operation;

p) the rotational motion limited to insure the angular acceleration and velocity do not cause deformation of the meniscus from a smooth parabolic shape;

q) the rotational motion of the container imparts a toroidal motion to the fluid in the container that will pull contaminating particles in the fluid toward the axis of rotation;

r) whereby image sensors are positioned relative to the axis of rotation of the container, whereby a focal point of detection coincides with the axis of rotation of the container so to view the content of the solution in the container and specifically the interior bottom center of the container with the illumination system providing a contrasting geometric size and shape of substantially all of the particles in the solution that have changed position in the image being identified, binary and grayscale information being recorded, particles evaluated and measured, and reporting the information of each particle on being displayed on a human machine interface.

2. An improved method for detection, measurement and determination of key characteristics of contaminating particles found in the solution within a container (1 ml to 50 ml) by placing substantially all particles within a predetermined size range, contained in the solution, into motion without turbulent flow using a precise velocity motion profile (VMP) designed specifically for causing the fluid contents of the container of a given size and shape, fluid surface tension, fluid viscosity and fill level to be set in motion, utilizing a programmable rotary motion device, an image processing computer for image acquisition, image storage and image processing capability for executing control software embodied on a computer readable medium, to provide the steps of:

a) use of a computer data file for extraction of key inspection features for a specific inspection parameters in a memory location referenced by a specific identification code that is unique to a container model or type that define the dimensions of the container, contents of the container, and the fill level of the container;

b) use of a computer data file for extraction of key inspection features for a specific inspection parameters in a memory location referenced by a specific identification code that is unique to a container model or type that define the dimensions of the container, contents of the container, and the fill level of the container;

c) storing one or more reference inspection mask images of a new master data file in a memory location referenced by a specific identification code that is unique to a container model or type that define the dimensions of the container, contents of the container, and the fill level of the container;

d) storing one or more rotary motion programs called velocity motion profiles (VMP) of a new master data file in a memory location referenced by a specific identification code that is unique to a container model or type that define the dimensions of the container, contents of the container, and the fill level of the container;

e) the velocity motion profile defines an acceleration, a maximum rotational velocity, a duration at maximum rotational velocity, followed by a deceleration to zero rotational velocity;

f) the velocity motion profile imposes a toroidal flow of the solution in the container; and g) the fluid flow generates negligible or no turbulence in the meniscus;

h) characterized in that motion is imposed on substantially all particles in solution with a mass equal to or less than, the upper limit particle mass defined by the velocity motion profile given the attributes of the container type parameters;

i) characterized in that motion is imposed on substantially all particles in solution with a size equal to or less than the upper limit particle size defined by the velocity motion profile given the attributes of the container type parameters;

j) one or more velocity motion profiles are utilized for the inspection for a specific container type, fluid content and fluid fill level;

k) acquisition of a test image of a sample referenced by a specific identification code that is unique to a container model or type that defines the dimensions of the container, contents of the container, and the fill level of the container and storage of the test image in memory;

l) determining the size and position of one or more inspection zones of the grayscale image as referenced by a specific identification code that is unique to a container model or type that defines the dimensions of the container, contents of the container, and the fill level of the container and storage of the inspection zones in memory;

m) multiple inspection zone are implemented simultaneously;

n) placement of a test container in the inspection position, excitation of the container with a specific velocity motion profile, acquisition of a sequence of images and storage of the images in the image processing computer at specific time from the start of the velocity motion profile or alternatively from the end of a velocity motion profile as required by the specific identification code that is unique to a container model or type that defines the dimensions of the container, contents of the container, and the fill level of the container;

o) creating and storage of a reference background image for the first 50% of acquired images by using the last acquired image in the total sequence of acquired images;

p) creating and storage of a reference background image for the last 50% of acquired images by using the first acquired image in the total sequence of acquired images;

q) creating a difference image by grayscale subtraction of a test image from the reference background image as determined in steps o) and p);

r) creating and storing in memory a list of values comprising grayscale objects representing resulting information in the difference image that are larger than a pre-determined criteria;

s) reducing the number of grayscale objects in the list created in step r) by applying pre-determined size and shape filtering algorithms and then storing in memory the remaining objects in a revised list;

t) containers that have objects on the revised list are defective and the image processing computer generates an error message prompting a user that the container tested is defective and requesting the removal of the container from acceptable product;

u) the inspection information from each test is displayed on a human machine interface and stored permanently on one of the internal storage hard drives or written to a recordable digital video disc for offsite record storage.

3. An improved method for the creating an instrument calibration curve that allows the correlation of the dimension of a particle contained in the solution of a transparent container (1 ml to 50 ml) as determined by image acquisition and processing to that of NIST traceable particles standards, within a specified size range, comprising the steps of:
  a) the movement of particles in the container whereby rotation of the container using a predefined velocity motion profile causing substantially all of the particles in the solution in the container to experience a change in position with a corresponding change in time;
  b) recording the properties of particles isolated in each defined inspection volume;
  c) determine the mean of the particle properties in each defined inspection volume over "n" images, primary properties included the geometric shape and integration of grayscale values over the geometric shape;
  d) evaluate the particle only if its properties lie within a specific range of the mean of "x" samples and establish a mean equivalent pixel width in each corresponding inspection volume;
  e) the generation of a calibration table by evaluating a series of NIST traceable dimensional standards in which the standards increase in diameter and recording the equivalent pixel width of the particle in each corresponding inspection volume;
  f) the generation of a calibration curve by plotting the pixel width on the x-axis and the NIST standard diameter on the y-axis to produce a linear equation in the form of $Y=mX+b$;
  g) one or more numerical calculations are performed to correlate particle size in pixels to equivalent physical dimension in micrometers using calibration curve established by measuring NIST traceable single seeded particle standards in each of the defined inspection volumes.

4. The method of claim 1, wherein the time required for the inspection, including image acquisition, image storage, image processing and analysis for each of the container's one or more defined inspection volumes is between 5 and 30 scan times; wherein a typical scan time is 30 to 60 milliseconds.

5. The method of claim 1, wherein the detection of contaminating particles is based on either a) light extinction that produces well-defined geometric shape(s) or b) grayscale shapes defined by the summation of grayscale values in an area defined by the approximate geometric shape.

6. The method of claim 5, wherein the aspect ratio of the grayscale shape is in a range of 0.8:1 to 1.2:1 and defined by geometric width and an equivalent number of pixels in the vertical dimension starting from the geometric top of the shape.

7. The method of claim 5, wherein the measurement of particles is confined to the defined inspection volumes, and is further confined to the front two-thirds of the container volume nearest to the detector, and is further confined to eliminating the extreme zones toward the far left and far right near the container walls that are more than 75 percent of the distance from the centerline of the container to the container walls.

8. The method of claim 7, wherein the measurement of small particles (low to medium mass, equivalent to $<=350\,\mu m$ diameter stainless steel spheres) is further confined to those particles in a defined inspection volume centered about the bottom center of the container, that is no more than 50 percent of the distance from the centerline of the container.

9. The method of claim 7, wherein the measurement of large (heavy mass, equivalent to $>350\,\mu m$ diameter stainless steel spheres) particles is further confined to those particles that travel from left to right in the images, assuming a counter-clockwise rotation of the container, in a defined inspection volume near the forward portion of the container and more than 75 percent of the distance from the centerline of the container.

10. The method of claim 7, wherein the measurement of light particles (low density $<=$density of the fluid) is further confined to those particles that move in the solution through an inspection volume centered in the container but not including the bottom of the container.

11. The method of claim 3, wherein a series individual NIST traceable spheres of known diameters, diameters range from 40 $\mu m$ to 400 $\mu m$, each sample placed in a thoroughly cleaned container, filled with WFI (ultra pure, Water for Injection) to the proper level, and measured to determine equivalent pixel diameters to generate a calibration curve to be used in conjunction with the bottom center inspection volume.

12. The method of claim 11, wherein the calibration curve is used to determine the equivalent diameter in micrometers of contaminating particles in other containers of the same shape, size and fluid fill level when said invention determines diameter in pixels.

13. The method of claim 2, wherein the utilization of a specific velocity motion profile (VMP) for a given container shape, size, fluid fill level, fluid viscosity imposes a toroidal flow causing separation of particles by mass, where the smaller particles are moved to the center of the container and the sensor has maximum focus to detect the smallest particles.

14. The method of claim 2, wherein the invention performs simultaneous independent evaluations of the near field and far field regions of the images and applies individual inspection criteria to each zone.

15. The method of claim 2, wherein the invention is used for counting the number or particles and determining the sizes of those particles in solution in the container, and creating a histogram of particle size verses number of particles in each bin on the human machine interface display.

16. The method of claim 15, wherein the invention is used to characterize the particle population in the 40 $\mu m$ to 1,000 $\mu m$ size range in a individual container or a set of containers.

17. The method of claim 3, wherein the method of using the mean of multiple measurements provides an accuracy improvement in determination of a contaminating particle size which is displayed on the human machine interface.

18. The method of claim 2, wherein large contaminating particles with a density greater than that of the fluid, such as glass shards, metal chips and debris can be detected and measured between 2 and 10 scans in the inspection volume that includes the bottom of the container and occurs within 300 milliseconds of the end of the velocity motion profile (VMP).

* * * * *